(12) United States Patent
Hirose et al.

(10) Patent No.: US 11,952,403 B2
(45) Date of Patent: Apr. 9, 2024

(54) POWDERED WHEAT PROTEIN AND METHOD FOR PRODUCING SAME

(71) Applicant: GLICO NUTRITION CO., LTD., Osaka (JP)

(72) Inventors: Tahiro Hirose, Osaka (JP); Koichiro Kinoshita, Osaka (JP); Tetsuya Murakami, Osaka (JP)

(73) Assignee: GLICO NUTRITION CO., LTD., Osaka (JP)

( * ) Notice: Subject to any disclaimer, the term of this patent is extended or adjusted under 35 U.S.C. 154(b) by 279 days.

(21) Appl. No.: 16/490,580

(22) PCT Filed: Mar. 6, 2018

(86) PCT No.: PCT/JP2018/008557
§ 371 (c)(1),
(2) Date: Sep. 2, 2019

(87) PCT Pub. No.: WO2018/164114
PCT Pub. Date: Sep. 13, 2018

(65) Prior Publication Data
US 2020/0071366 A1 Mar. 5, 2020

(30) Foreign Application Priority Data
Mar. 7, 2017 (JP) .................................. 2017-043287

(51) Int. Cl.
*C07K 14/415* (2006.01)
*A23J 3/18* (2006.01)
*A23L 7/109* (2016.01)

(52) U.S. Cl.
CPC ............... *C07K 14/415* (2013.01); *A23J 3/18* (2013.01); *A23L 7/109* (2016.08); *A23V 2002/00* (2013.01)

(58) Field of Classification Search
None
See application file for complete search history.

(56) References Cited

U.S. PATENT DOCUMENTS 3,925,343 A * 12/1975 Hampton .................. A23J 3/18
426/656
4,871,577 A * 10/1989 Endo ...................... A21D 2/265
426/653
5,138,038 A  8/1992 Katayama et al.
5,273,773 A  12/1993 Katayama et al.
(Continued)

FOREIGN PATENT DOCUMENTS

JP  5216393 A  2/1977
JP  53130450 A  11/1978
(Continued)

OTHER PUBLICATIONS

English translation of JP 2007000046 to Kitagawa et al. Publication date Jan. 11, 2007. pp. 1-13. (Year: 2007).*
(Continued)

*Primary Examiner* — Jenna A Watts
(74) *Attorney, Agent, or Firm* — Renner, Otto, Boisselle & Sklar, LLP

(57) ABSTRACT

A powdered wheat protein that can achieve both a high dough-formation speed and a high bulk density is obtained by drying a pasty raw material formed by kneading a wheat protein, an acid, and water, by flash drying or freeze drying.

8 Claims, 8 Drawing Sheets

(56) References Cited

U.S. PATENT DOCUMENTS

| | | |
|---|---|---|
| 5,274,079 A | 12/1993 | Katayama et al. |
| 5,366,661 A | 11/1994 | Katayama et al. |
| 2005/0287267 A1 | 12/2005 | Manigat |
| 2008/0254200 A1 | 10/2008 | Bassi et al. |
| 2010/0145019 A1 | 6/2010 | Adachi et al. |
| 2015/0250204 A1 | 9/2015 | Bassi et al. |

FOREIGN PATENT DOCUMENTS

| | | |
|---|---|---|
| JP | 01014274 A | 1/1989 |
| JP | 2001161294 A | 6/2001 |
| JP | 2007000046 A | 1/2007 |
| JP | 2010523148 A | 7/2010 |
| WO | 2009011253 A1 | 1/2009 |
| WO | 2016125599 A1 | 8/2016 |

OTHER PUBLICATIONS

NPL relating to conversion of molarity and molality of organic acid solutions. Available online as of Aug. 31, 2021 from https://www.toppr.com. pp. 1-6. (Year: 2021).*

English Translation of ISR of corresponding application PCT/JP2018/008557 dated May 22, 2018.

Murakami, T. et al., "Dispersion in the Presence of Acetic Acid or Ammonia Confers Gliadin-Like Characteristics to the Glutenin in Wheat Gluten", 2015, J. Food Sci., vol. 80, No. 2, pp. C269-C278.

Murayama, Takeshi, "Properties of Wheat Protein and Processed Gluten and their Utilization to Foods", 1986, New Food Industry, vol. 27, No. 7, pp. 17-24.

Extended European Search Report for corresponding European application No. EP 18763481 dated Jul. 10, 2020.

* cited by examiner

EXAMPLE2

COMPARATIVE EXAMPLE2-1

COMPARATIVE EXAMPLE2-2

EXAMPLE3-1

EXAMPLE3-2

EXAMPLE3-3

EXAMPLE3-4

EXAMPLE3-5

EXAMPLE3-6

EXAMPLE3-7

EXAMPLE3-8

EXAMPLE3-9

EXAMPLE3-10

EXAMPLE3-11

EXAMPLE3-12

POWDERED WHEAT PROTEIN AND METHOD FOR PRODUCING SAME

This application is a national phase of International Application No. PCT/JP2018/008557 filed Mar. 6, 2018, and claims priority to Japanese Application No. 2017-043287 filed on Mar. 7, 2017, which is incorporated herein by reference.

TECHNICAL FIELD

The present invention relates to a powdered wheat protein that achieves a high dough-formation speed and a high bulk density. The present invention also relates to a method for producing the powdered wheat protein.

BACKGROUND ART

Wheat proteins, which are supplied in abundant quantities as by-products in the production of wheat starch, are known to exhibit physical properties such as extensibility, water absorbency, cohesion, and viscoelasticity, and are used in various processed foods. The wheat proteins (wheat gluten) can be obtained by washing, with water, dough obtained by kneading wheat flour, and washing away starch. The wheat proteins in this state are in the form of a gummy mass containing moisture, called wet gluten. Because the wheat proteins in the state of wet gluten are inconvenient in terms of distribution or preservability, powdered wheat proteins (vital gluten) obtained by drying wet gluten are generally in widespread use.

Conventionally, the powdered wheat proteins are known to be produced by a method in which a dispersion of wheat gluten is dried by spray drying or freeze drying (hereinafter "the spray drying or freeze drying method"), or a method in which wet gluten and dusting flour (such as vital gluten) are mixed, and the mixture is dried by the flash drying method (hereinafter "the flash drying method").

Regarding the spray drying or freeze drying method, various techniques for modifying the physical properties of the wheat proteins or enhancing the production efficiency have been proposed. For example, Patent Literature 1 discloses that an isolated wheat protein composition that is substantially free of sulfites is obtained by mixing water, an acid, and wheat gluten to form a gluten slurry, and agitating and drying the gluten slurry. Moreover, Patent Literature 2 discloses that low-foamability surface-active action can be imparted to a wheat protein, by subjecting the wheat protein to a hydrolysis treatment with an alkali and a degradation treatment with an acid, an enzyme, an oxidizing agent, or a reducing agent. Furthermore, Patent Literature 3 discloses that a vital gluten hydrolysate can be efficiently obtained by dispersing gluten in a solution containing a galacturonic acid-containing water-soluble polysaccharide, and drying the dispersion.

While the powdered wheat proteins obtained by the spray drying or freeze drying method are advantageous in that the dough-formation speed is high, they are disadvantageous in that the powder volume is increased, compared to that of powdered wheat proteins obtained by the flash drying method. This causes an increase in transport costs due to a decrease in the mass per unit volume, reduced workability during mixing of powders due to a difference in bulk density, and the like. Even Patent Literatures 1 to 3 which disclose the spray drying or freeze drying method nowhere contemplate a method for producing a powdered wheat protein having an increased bulk density.

On the other hand, while the powdered wheat proteins obtained by the flash drying method have a high bulk density, they are disadvantageous in that the dough-formation speed is low.

If a powdered wheat protein could be provided that has both the advantage of the spray drying or freeze drying method and the advantage of the flash drying method, i.e., a powdered wheat protein that achieves a high bulk density and a high dough-formation speed, it would be possible to provide a food ingredient that has high market value and is highly convenient. In the prior art, however, no techniques have been developed for producing a powdered wheat protein having such properties.

CITATION LIST

Patent Literature

Patent Literature 1: JP 2010-523148 A
Patent Literature 2: JP H01-14274 A
Patent Literature 3: WO 2009/011253

SUMMARY OF INVENTION

Technical Problem

An object of the present invention is to provide a powdered wheat protein that achieves a high dough-formation speed and a high bulk density, and a method for producing the same.

Solution to Problem

As a result of extensive research to solve the above-mentioned problem, the present inventors have found that a powdered wheat protein that can achieve both a high dough-formation speed and a high bulk density is obtained by drying a pasty raw material formed by kneading a wheat protein, an acid, and water, by freeze drying or flash drying. The present inventors have also found that the powdered wheat protein has a loose bulk density of 40 g/100 cm$^3$, and has a time to reach the maximum consistency of 5 minutes or less in a mixograph test under specific conditions, and has properties different from those of conventional powdered wheat proteins. The present invention has been completed by conducting further research based on these findings.

In summary, the present invention provides the following aspects of invention.

Item 1. A powdered wheat protein having a loose bulk density of 40 g/100 cm$^3$ or more, and having a time to reach the maximum consistency of 5 minutes or less in a mixograph test under the following conditions:

<conditions for the mixograph test>

10 g of the powdered wheat protein, 20 g of acetylated wheat starch (degree of substitution (DS): 0.02), and 28 g of water (15° C.) are kneaded at a temperature of 25° C., using a 35-g mixograph (stirring-type viscoelasticity measuring apparatus), based on the AACC method 54-40.02 defined by AACC (American Association of Cereal Chemists), and consistency of the resulting material is measured with time.

Item 2. The powdered wheat protein according to item 1, wherein a packed bulk density is 60 g/100 cm$^3$ or more.

Item 3. The powdered wheat protein according to item 1 or 2, wherein in the mixograph test under said conditions, a gradient$_{(Max-After\ 5\ min)}$ calculated based on the following equation, using a consistency at the time to reach the maximum consistency ($V_{max}$) and a consistency at 5 minutes after the time to reach the maximum consistency ($V_{5\ min\ after\ Xmax}$), is −2.00 tq %/minute or less:

$$\text{gradient}_{(Max\text{-}After\ 5\ min)} = (V_{max} - V_{5\ min\ after\ Xmax})/5 \quad \text{[Expression 1]}$$

Item 4. A processed food comprising the powdered wheat protein according to any one of items 1 to 3.

Item 5. The processed food according to item 4, which is a noodle.

Item 6. A method for producing a powdered wheat protein comprising:

step 1 of preparing a pasty raw material formed by kneading a wheat protein, an acid, and water; and step 2 of drying the pasty raw material obtained in step 1 by freeze drying or flash drying.

Item 7. The method for producing a powdered wheat protein according to item 6, wherein the pasty raw material obtained in step 1 is allowed to stand for 5 minutes or more, and then subjected to step 2.

Item 8. The method for producing a powdered wheat protein according to item 6 or 7, wherein an acid content in the pasty raw material prepared in step 1 is 0.01 to 0.50 mol/kg.

Item 9. The method for producing a powdered wheat protein according to any one of items 6 to 8, wherein a moisture content in the pasty raw material prepared in step 1 is 70% by mass or less.

Advantageous Effects of Invention

The powdered wheat protein of the present invention has a bulk density comparable to or higher than that of powdered wheat proteins obtained by the flash drying method, and thus, can achieve savings in transport costs, a reduction in storage space, improved workability during use, and the like.

Figure 1A:
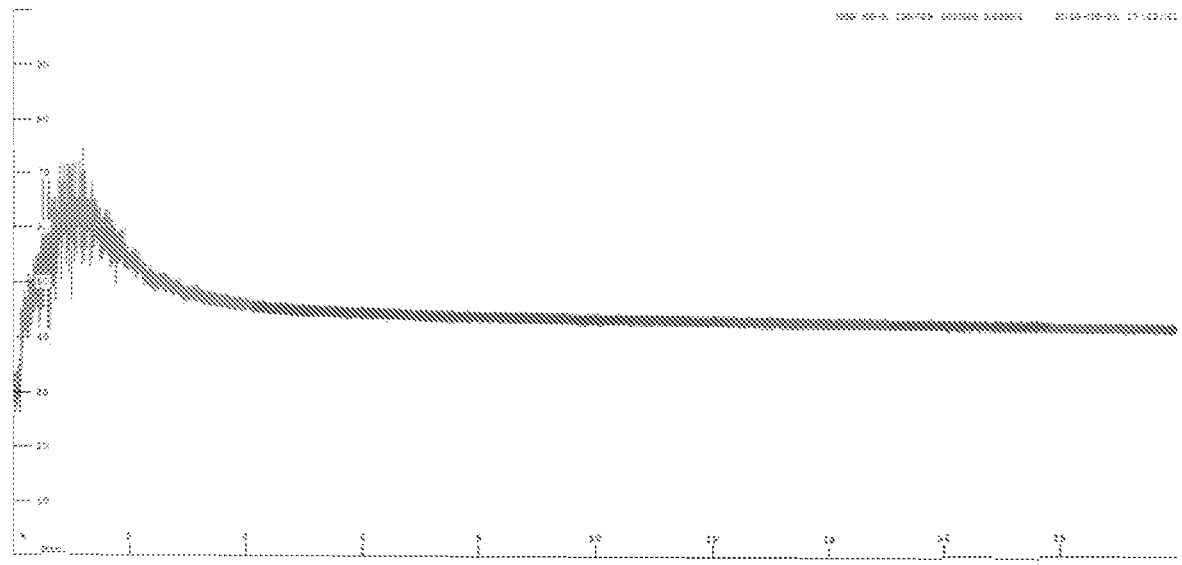
FIG. 1A shows the results of measuring changes with time in consistency by a mixograph test, for the powdered wheat proteins of Example 2, and Comparative Examples 2-1 and 2-2.

Moreover, because the powdered wheat protein of the present invention has a high dough-formation speed, it can also achieve a reduction in production time, labor savings, and the like in the production of various types of processed foods.

Furthermore, in one preferred embodiment of the powdered wheat protein of the present invention, good extensibility can be imparted in the formation of a dough. This can improve, for example, the dough-binding ability when unheated in various processed foods made from doughs, and the gas-retaining ability for a gas produced by fermentation in foods that involve fermentation.

DESCRIPTION OF EMBODIMENTS

The powdered wheat protein of the present invention is characterized by having a loose bulk density of 40 g/100 cm$^3$ or more, and having a time to reach the maximum consistency of 5 minutes or less in a mixograph test under specific conditions. The powdered wheat protein of the present invention will be hereinafter described in detail.

[Bulk Density]

The powdered wheat protein of the present invention has a loose bulk density of 40 g/100 cm$^3$ or more. Because the powdered wheat protein of the present invention has such a high loose bulk density, it can achieve savings in transport costs and a reduction in storage space, and can prevent the workability from being reduced during mixing of the powder with other powder material. The loose bulk density of the powdered wheat protein of the present invention is preferably 40 to 80 g/100 cm$^3$, more preferably 40 to 60 g/100 cm$^3$, and particularly preferably 50 to 60 g/100 cm$^3$.

As used herein, the loose bulk density refers to a value determined by adding the powdered wheat protein into a cylindrical container having a volume of 100 cm$^3$ (height outer diameter: 5.4 cm, bottom inner diameter: 2.44 cm, area: 18.7 cm$^2$) slowly over 1 minute, and measuring the mass of the powdered wheat protein loaded into the container. More specifically, the loose bulk density can be measured using the A.B.D. Powder Property Measuring Apparatus (Tsutsui Scientific Instruments Co., Ltd.).

Moreover, in one embodiment of the powdered wheat protein of the present invention, the packed bulk density is 60 g/100 cm$^3$ or more. When the packed bulk density is within this range, a powdered wheat protein having even superior handleability can be provided. The packed bulk density of the powdered wheat protein of the present invention is preferably 60 to 100 g/100 cm³, more preferably 60 to 80 g/100 cm³, and particularly preferably 65 to 75 g/100 cm³.

As used herein, the packed bulk density refers to a value determined by loading the powdered wheat protein into a cylindrical container having a volume of 100 cm³ (height outer diameter: 5.4 cm, bottom inner diameter: 2.44 cm, area: 18.7 cm²) while tapping once in 1 second for 2 minutes, and measuring the mass of the powdered wheat protein loaded into the container. More specifically, the packed bulk density can be measured using the A.B.D. Powder Property Measuring Apparatus (Tsutsui Scientific Instruments Co., Ltd.).

[Physical Properties Measured by Mixograph Test]

The powdered wheat protein of the present invention exhibits a time to reach the maximum consistency of 5 minutes or less in a mixograph test under the conditions shown below. Because the powdered wheat protein of the present invention has such a property, the dough-formation speed can be increased. As a physical property of the powdered wheat protein of the present invention, the time to reach the maximum consistency is preferably 4 minutes or less, more preferably 1 to 3 minutes, and particularly preferably 1 to 2 minutes.

As used herein, the time to reach the maximum consistency in a mixograph test refers to the time from the start of the mixograph test until the time when the powdered wheat protein exhibits the maximum consistency.

Moreover, as a preferred property of the powdered wheat protein of the present invention, in the mixograph test under the conditions shown below, a gradient$_{(Max\text{-}After\ 5\ min)}$ calculated based on the following equation, using a consistency at the time to reach the maximum consistency ($V_{max}$) and a consistency at 5 minutes after the time to reach the maximum consistency ($V_{5\ min\ after\ Xmax}$), is −2.0 tq %/minute or less. When the powdered wheat protein of the present invention has such a property, the dough to be formed can be controlled, depending on the mixing time, to range from a firm one to a soft one, to produce doughs having various degrees of firmness. As a physical property of the powdered wheat protein of the present invention, the gradient$_{(Max\text{-}After\ 5\ min)}$ is preferably −2.5 tq %/minute or less, more preferably −2.5 to −5.0 tq %/minute, and particularly preferably −2.5 to −4.5 tq %/minute. In the unit "tq %/minute" of the gradient$_{(Max\text{-}After\ 5\ min)}$, the numerator represents the mixing resistance (tq %), and the denominator represents the time (minute).

$$\text{gradient}_{(Max\text{-}After\ 5\ min)}=(V_{max}-V_{5\ min\ after\ Xmax})/5 \quad \text{[Expression 2]}$$

The conditions for the mixograph test in the present invention are as follows: 10 g of the powdered wheat protein to be measured, 20 g of acetylated wheat starch (degree of substitution (DS): 0.02), and 28 g of water (15° C.) are kneaded at a temperature of 25° C., using a 35-g mixograph (stirring-type viscoelasticity measuring apparatus), based on the AACC method 54-40.02 defined by AACC (American Association of Cereal Chemists), and the consistency is measured with time.

[Extensibility During Dough Formation]

In one preferred embodiment of the powdered wheat protein of the present invention, the powdered wheat protein has excellent extensibility in the formation of a dough. More specifically, in one preferred embodiment of the powdered wheat protein of the present invention, the extension distance to break of the dough as measured under the conditions shown below is 22 mm or more, preferably 23 mm or more, more preferably 24 mm or more, and particularly preferably 27 mm or more. When the extension distance is set in this range, the dough-binding ability when unheated in various processed foods made from doughs can be improved, and the gas-retaining ability for a gas produced by fermentation in foods that involve fermentation can be improved. As a result, the convenience during the production of processed foods can be enhanced.

<Conditions for Testing Extension Distance to Break of Dough>

A dough is formed by adding, to 100 g of the powdered wheat protein to be measured, 0.01 times as much sodium chloride and 1.5 times as much ion-exchange water in terms of mass ratio, and kneading the mixture in a mixer for 10 minutes. Next, from the obtained dough, a specimen having a length of 53 mm, a height of 5 mm, and a width of 5 mm is prepared and allowed to stand at 25° C. for 30 minutes. Thereafter, using a texture analyzer, a tensile test is performed at 25° C. and at a tensile speed of 3.30 mm/second and a distance between the grips of 400 mm, and the distance of movement of the grips when the specimen is broken is determined as the extension distance.

More specifically, the extension distance to break of the dough can be readily determined by using a texture analyzer (Kieffer Dough & Gluten Extensibility Rig; manufactured by Stable Micro Systems) accompanied with a dough molding form and press. The method for measuring the extension distance using the texture analyzer is as follows: From a dough formed as described above using the dough molding form and press accompanying the texture analyzer, a specimen having the above-mentioned dimensions is prepared and allowed to stand at 25° C. for 30 minutes. Thereafter, using the texture analyzer, a tensile test is performed at 25° C., a tensile speed of 3.30 mm/second, a distance between the grips of 400 mm, and a trigger load of 5.0 g, and the extension distance at the time when the specimen is broken is determined.

[Production Method]

The method for producing the powdered wheat protein of the present invention is not particularly limited as long as the powdered wheat protein produced can have the above-described properties; specifically, preferred examples include a method including the following steps 1 and 2:

Step 1: preparing a pasty raw material formed by kneading a wheat protein, an acid, and water.

Step 2: drying the pasty raw material obtained in step 1 by freeze drying or flash drying.

In accordance with the production method including steps 1 and 2, the powdered wheat protein produced can also be imparted with extensibility in the formation of a dough, as described above. Regarding the method for producing the powdered wheat protein of the present invention including steps 1 and 2, each of the steps will be hereinafter described.

(Step 1)

In step 1, a pasty raw material formed by kneading a wheat protein, an acid, and water is prepared. As used herein, the pasty raw material refers to a raw material that has flowability and is pasty.

The wheat protein used as an ingredient in step 1 may be wet gluten extracted from wheat, or may be vital gluten obtained by drying the wet gluten. Preferred examples of the wheat protein to be used as an ingredient include raw wheat gluten.

While the acid to be used in step 1 may be an organic or inorganic acid as long as it is usable in the production of foods, examples include organic acids, such as acetic acid, citric acid, lactic acid, malic acid, tartaric acid, fumaric acid, succinic acid, gluconic acid, and adipic acid; and inorganic acids, such as hydrochloric acid, phosphoric acid, carbonic acid, and sulfuric acid. Among these acids, acetic acid, lactic acid, and the like are preferable. These acids may be used alone or in combination.

In step 1, the pasty raw material may be prepared by adding the wheat protein, the acid, and water individually, and kneading them, or by mixing the acid and water in advance to prepare an aqueous acid solution, and then adding the aqueous acid solution to the wheat protein, and kneading them.

In the pasty raw material prepared in step 1, the wheat protein constitutes about 75% by weight or more of the remainder excluding the acid and water.

While the amount of the acid to be used in step 1 is not particularly limited, for example, the acid content in the prepared pasty raw material may be adjusted to 0.01 to 0.50 mol/kg, preferably 0.05 to 0.30 mol/kg, and still more preferably 0.05 to 0.25 mol/kg. When the pasty raw material is prepared by adding this amount of the acid, the powdered wheat protein of the present invention can be efficiently produced.

While the amount of water to be used in step 1 is not particularly limited as long as the pasty raw material is prepared, for example, the moisture content in the prepared pasty raw material may be adjusted to 65% by mass or less, preferably 15 to 65% by mass, still more preferably 20 to 60% by mass, and particularly preferably 30 to 45% by mass. If the final moisture content is about 80% by mass or more, the finally obtained raw material will become liquid, and the powdered wheat protein of the present invention cannot be obtained.

In addition to the wheat protein, the acid, and water, the pasty raw material prepared in step 1 may optionally include additives, such as redox agents, oxidoreductases, and salts. While these additives are not particularly limited as long as they are usable in the production of foods, examples include redox agents, such as sodium bisulfite, sodium hypochlorite, and cysteine-containing peptides; oxidoreductases, such as glucose oxidase and ascorbate oxidase; and salts, such as sodium phosphate, sodium citrate, and sodium chloride.

The temperature during kneading of the ingredients in step 1 is, for example, 10 to 45° C., preferably 20 to 45° C., more preferably 30 to 45° C., and particularly preferably 30 to 45° C., although not particularly limited thereto.

Moreover, in the preparation of the pasty raw material formed by kneading the wheat protein, the acid, and water in step 1, a kneading machine such as a static mixer, a kneader, or a vertical mixer, for example, may be used.

The time for kneading the ingredients in step 1 does not greatly affect the properties of the powdered wheat protein obtained after step 2, and thus, may be appropriately adjusted depending on the amount of the pasty raw material to be prepared, the type of the apparatus for kneading, and the like. For example, the kneading time is 1 minute or more, preferably 1 to 30 minutes, more preferably 1 to 20 minutes, and particularly preferably 1 to 15 minutes.

While the pasty raw material prepared by step 1 may be directly subjected to step 2, it is preferably allowed to stand for 5 minutes or more, and then subjected to step 2. In this manner, when the prepared pasty raw material is allowed to stand temporarily, and then subjected to step 2, the gradient$_{(Max-After\ 5\ min)}$ in the mixograph test can be set in the above-described range in the powdered wheat protein obtained after step 2, and the powdered wheat protein can be imparted with even superior physical properties.

When the pasty raw material prepared by step 1 is allowed to stand before being subjected to step 2, the standing time may be 5 minutes or more; however, from the viewpoint of setting the gradient$_{(Max-After\ 5\ min)}$ in the mixograph test in an even more preferred range in the powdered wheat protein obtained after step 2, the standing time is preferably 8 minutes or more, more preferably 8 to 30 minutes, particularly preferably 10 to 30 minutes, and most preferably 10 to 20 minutes.

The temperature during which the pasty raw material prepared by step 1 is allowed to stand temporarily may be appropriately adjusted in the range of temperatures where the wheat protein contained as an ingredient is not denatured; for example, the temperature is 10 to 45° C., preferably 20 to 45° C., more preferably 30 to 45° C., and particularly preferably 35 to 40° C.

(Step 2)

In step 2, the pasty raw material obtained in step 1 is dried by freeze drying or flash drying. In this manner, by making the pasty raw material obtained in step 1 into a powder by freeze drying or flash drying, the powdered wheat protein of the present invention having the above-described properties can be obtained.

Drying in step 2 may be performed until the pasty raw material becomes powdery. More specifically, drying in step 2 may be performed until the moisture content in the resulting powdered wheat protein becomes 12% by mass or less, preferably 10% by mass or less, and more preferably 8% by mass or less.

The powdered wheat protein obtained by step 2 may be optionally subjected to a grinding treatment, a particle-size regulation treatment, or the like to regulate the particle size.

[Applications of Powdered Wheat Protein]

The powdered wheat protein of the present invention can be used for various applications similar to those of conventional wheat proteins. In particular, as with conventional wheat proteins, the powdered wheat protein of the present invention has properties such as extensibility, water absorbency, cohesion, and viscoelasticity, and thus, is suitably used as a food ingredient to be added to processed foods.

The types of processed foods to which the powdered wheat protein of the present invention can be added include, although not particularly limited to, processed foods prepared from doughs mainly made from wheat flour, such as udon noodles (noodles made of wheat flour), Chinese noodles, gyoza (meat and vegetable dumplings) skin, shaomai (steamed meat dumplings) skin, spring roll skin, yaki-fu (baked wheat gluten), nama-fu (raw wheat gluten), and fu-manju (wheat gluten dumplings); fermented dough foods, such as bread, Chinese dumplings, and yeast doughnuts; sweets, such as sponge cakes, cookies, biscuits, caramels, puddings, and jellies; fat and oil processed foods, such as margarine, mayonnaise, shortening, whipped cream, flour pastes, and dressings; processed seafood/livestock products, such as kamaboko (boiled fish pastes), hams, and sausages; batters of deep-fried foods, such as tempura, fried chicken, and fried foods; fillings for deep-fried foods, and fillings for Chinese dumplings, gyoza, shaomai, spring rolls, sandwiches, and the like; seasonings, such as sauces, dipping sauces, and jams; dairy products, such as processed milk and fermented milk; various frozen foods; frozen desserts, such as ice creams and sherbets; and the like.

The powdered wheat protein of the present invention achieves a high dough-formation speed, and moreover, in one preferred embodiment, the powdered wheat protein of the present invention can improve the extensibility of the dough. In view of these properties of the powdered wheat protein of the present invention, the processed foods to which the powdered wheat protein of the present invention can be added are preferably processed foods prepared from doughs mainly made from wheat flour, or fermented dough foods, and more preferably noodles (such as udon noodles and Chinese noodles).

The content of the powdered wheat protein of the present invention in a processed food is not particularly limited, and may be appropriately adjusted depending on the type of the processed food and the like; for example, it is about 1 to 10% by mass, and preferably about 2 to 5% by mass.

EXAMPLES

The present invention will be hereinafter described in detail with reference to examples, although the present invention is in no way limited thereto.

Test Example 1

1. Production of Powdered Wheat Proteins

A dough was prepared by adding water to commercially available wheat flour (moisture: 13.0% by mass, ash: 0.5% by mass, protein: 13.0% by mass) and mixing. The dough was allowed to stand in water for 30 minutes, and then kneaded in the water to wash away starch to obtain viscoelastic wet gluten. The wet gluten had a moisture content of 64.4% by mass, and a protein content of 76.3% by mass on a dry-matter mass basis.

To 100 g of the wet gluten obtained above, an aqueous acid solution containing 0.11 mol/L of lactic acid and 0.13 mol/L of acetic acid was added to give each of the final moisture contents shown in Table 1, and the mixture was kneaded for 15 minutes using a vertical mixer, to obtain a pasty or liquid raw material. The resulting pasty or liquid raw material was allowed to stand at 30° C. for 10 minutes. The pasty or liquid raw material after being allowed to stand was quickly frozen and dried by freeze drying, and then made into a powder using a grinding machine to obtain a powdered wheat protein.

2. Measurement of Bulk Densities

The loose bulk density and the packed bulk density were measured for each of the obtained powdered wheat proteins. The method for measuring each of the bulk densities was as follows: The measurement of loose bulk density was performed using the A.B.D. Powder Property Measuring Apparatus (Tsutsui Scientific Instruments Co., Ltd.), by adding the powdered wheat protein into a cylindrical container having a volume of 100 cm$^3$ (height outer diameter: 5.4 cm, bottom inner diameter: 2.44 cm, area: 18.7 cm$^2$) slowly over 1 minute, and measuring the mass of the powdered wheat protein loaded into the container. The measurement of packed bulk density was performed using the A.B.D. Powder Property Measuring Apparatus (Tsutsui Scientific Instruments Co., Ltd.), by loading the powdered wheat protein into a cylindrical container having a volume of 100 cm$^3$ (height outer diameter: 5.4 cm, bottom inner diameter: 2.44 cm, area: 18.7 cm$^2$) while tapping once in 1 second for 2 minutes, and measuring the mass of the powdered wheat protein loaded into the container.

3. Results

Table 1 shows the results of measuring the loose bulk density and the packed bulk density for each powdered wheat protein. The results have revealed that in the powdered wheat proteins obtained by allowing the pasty raw material to stand for a certain time and then freeze-drying the pasty raw material, the loose bulk density is high, i.e., 40 g/100 cm$^3$ or more, and the bulkiness is effectively reduced, compared to that in the powdered wheat protein obtained by freeze-drying the liquid raw material (prior art). Note that the mixograph test shown in Test Example 2 below was performed on the powdered wheat proteins of Examples 1-1 to 1-9. As a result, in all the powdered wheat proteins, the time to reach the maximum consistency was 5 minutes or less.

TABLE 1

|  | Moisture Content (% by mass) in Raw Material Subjected to Freeze Drying | Form of Raw Material Subjected to Freeze Drying | Bulk Densities (g/100 cm$^3$) | |
|---|---|---|---|---|
|  |  |  | Loose Bulk Density | Packed Bulk Density |
| Example 1-1 | 15 | Pasty | 50.7 | 76.6 |
| Example 1-2 | 20 | Pasty | 49.4 | 78.1 |
| Example 1-3 | 30 | Pasty | 62.8 | 81.8 |
| Example 1-4 | 35 | Pasty | 56.0 | 68.5 |
| Example 1-5 | 40 | Pasty | 60.8 | 80.1 |
| Example 1-6 | 45 | Pasty | 57.4 | 73.9 |
| Example 1-7 | 50 | Pasty | 53.6 | 73.0 |
| Example 1-8 | 55 | Pasty | 43.6 | 64.5 |
| Example 1-9 | 60 | Pasty | 44.3 | 64.1 |
| Comparative Example 1 | 70 | Liquid | 35.7 | 53.9 |

Test Example 2

1. Production of Powdered Wheat Protein

A powdered wheat protein was produced using an actual machine used for industrial production. More specifically, to 100 Kg of wet gluten prepared using the same method as that in Test Example 1 above, an acid solution containing 11 mol/L of lactic acid and 18 mol/L of acetic acid was added to impart a final pH of 4.5±0.2 to the wet gluten, and the mixture was kneaded for 1 minute using a static mixer to obtain a pasty raw material. The resulting pasty raw material was allowed to stand at 40° C. for 5 minutes. The pasty raw material after being allowed to stand was dried by flash drying, and then made into a powder using a grinding machine to obtain a powdered wheat protein (Example 2).

For comparison, a commercially available powdered wheat protein produced by drying by flash drying (Comparative Example 2-1) and a commercially available powdered wheat protein produced by drying by spray drying (Comparative Example 2-2) were also prepared.

2. Measurement of Bulk Densities

For each of the powdered wheat proteins, the loose bulk density and the packed bulk density were measured using the same method as that in Test Example 1 above.

3. Mixograph Test

A mixograph test was performed on each of the powdered wheat proteins to determine the time to reach the maximum consistency. Moreover, the consistency at the time to reach the maximum consistency and the consistency at 5 minutes after the time to reach the maximum consistency were determined, and the gradient$_{(Max\text{-}After\ 5\ min)}$ was calculated according to the equation above. The conditions for the mixograph test were as follows:

10 g of the powdered wheat protein, 20 g of acetylated wheat starch (degree of substitution (DS): 0.02), and 28 g of deionized water (15° C.) were mixed at a temperature of 25° C., using a 35-g mixograph (NATIONAL MFG Co.), based on the AACC method 54-40.02 defined by AACC, and the consistency was measured with time.

4. Measurement of Dough Physical Properties

A dough was formed by adding, to the powdered wheat protein, 0.01 times as much sodium chloride and 1.5 times as much purified water in terms of mass ratio, and kneading the mixture in a mixer for 10 minutes. Next, from 60 g of the dough, a specimen having a length of 53 mm, a height of 5 mm, and a width of 5 mm was prepared using a dough molding form and press accompanying a texture analyzer (Kieffer Dough & Gluten Extensibility Rig; manufactured by Stable Micro Systems) and placed, and then allowed to stand at 25° C. for 30 minutes. Thereafter, using the texture analyzer, a tensile test was performed at 25° C., a tensile speed of 3.30 mm/second, a distance between the grips of 400 mm, and a trigger load of 5.0 g, and the distance of movement of the grips when the specimen was broken was determined as the extension distance.

3. Results

Figure 1B:
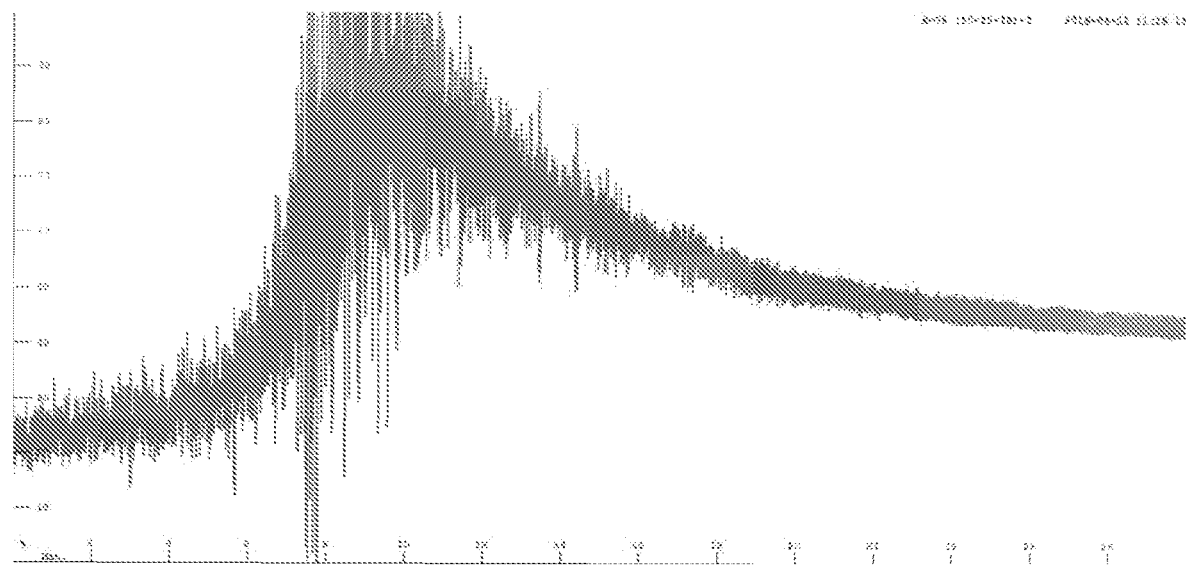
FIG. 1B shows the results of measuring changes with time in consistency by a mixograph test, for the powdered wheat proteins of Comparative Example 2-1.
Figure 1C:
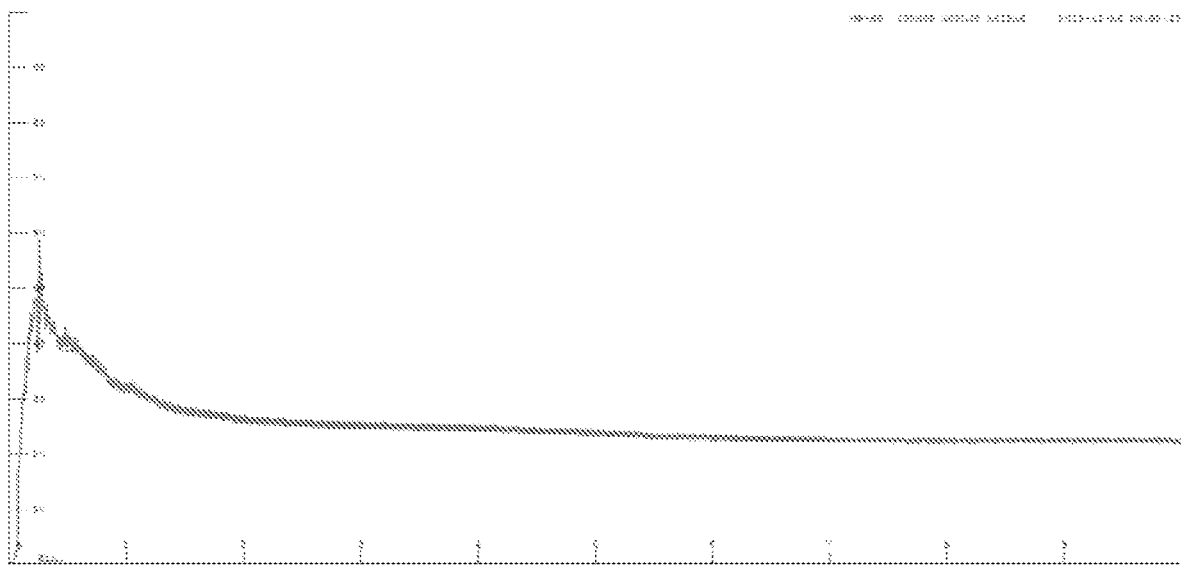
FIG. 1C shows the results of measuring changes with time in consistency by a mixograph test, for the powdered wheat proteins of Comparative Example 2-2.
Figure 2A:
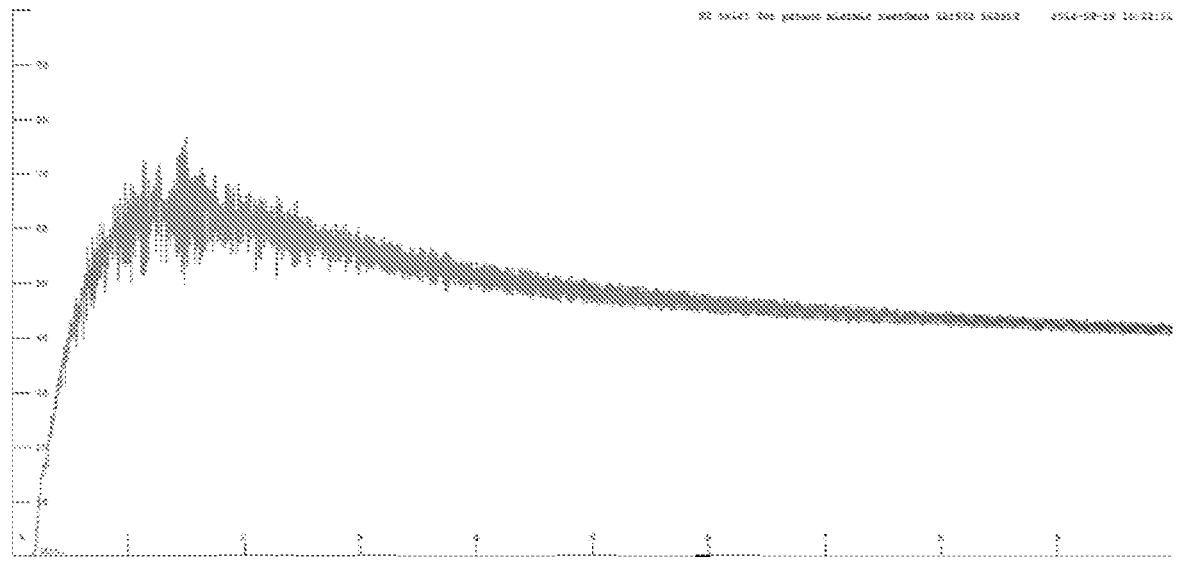
FIG. 2A shows the results of measuring changes with time in consistency by a mixograph test, for the powdered wheat proteins of Example 3-1.
Figure 2B:
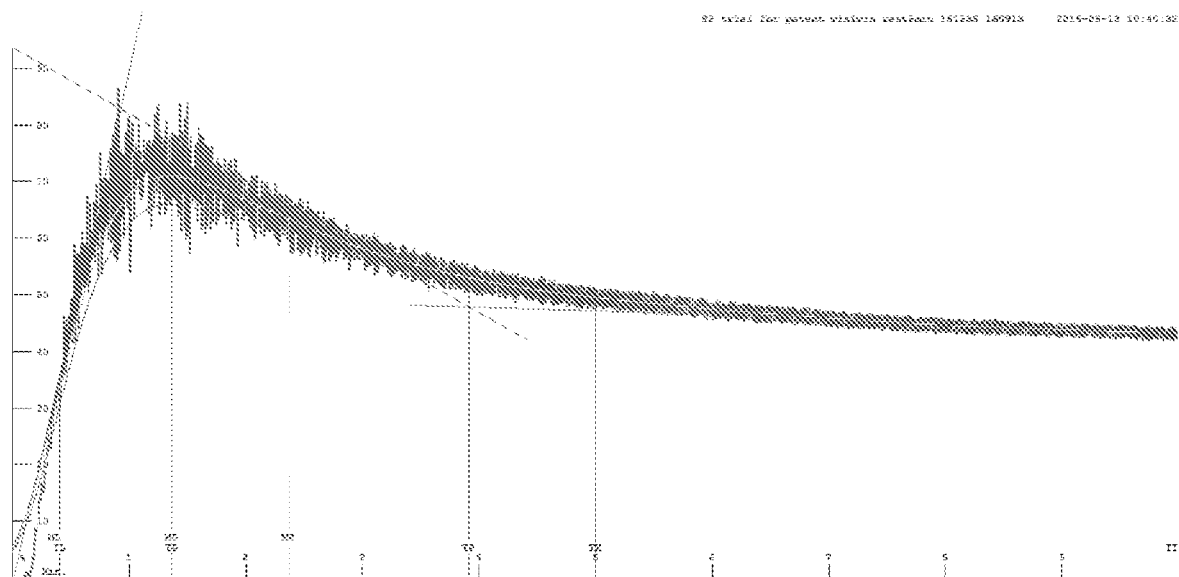
FIG. 2B shows the results of measuring changes with time in consistency by a mixograph test, for the powdered wheat proteins of Example 3-2.
Figure 2C:
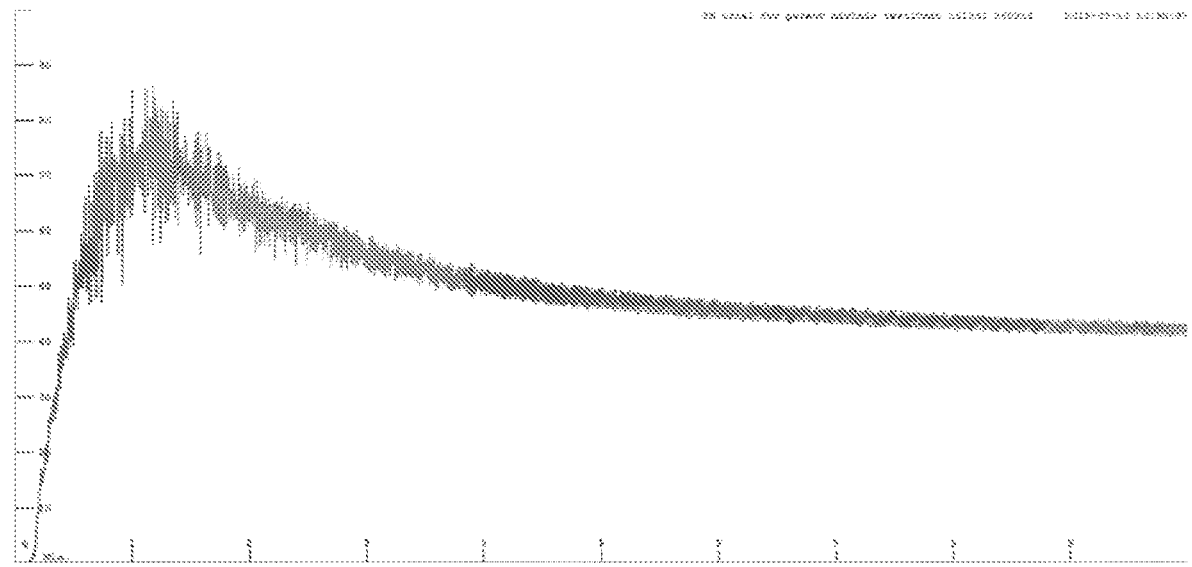
FIG. 2C shows the results of measuring changes with time in consistency by a mixograph test, for the powdered wheat proteins of Example 3 -3.
Figure 2D:
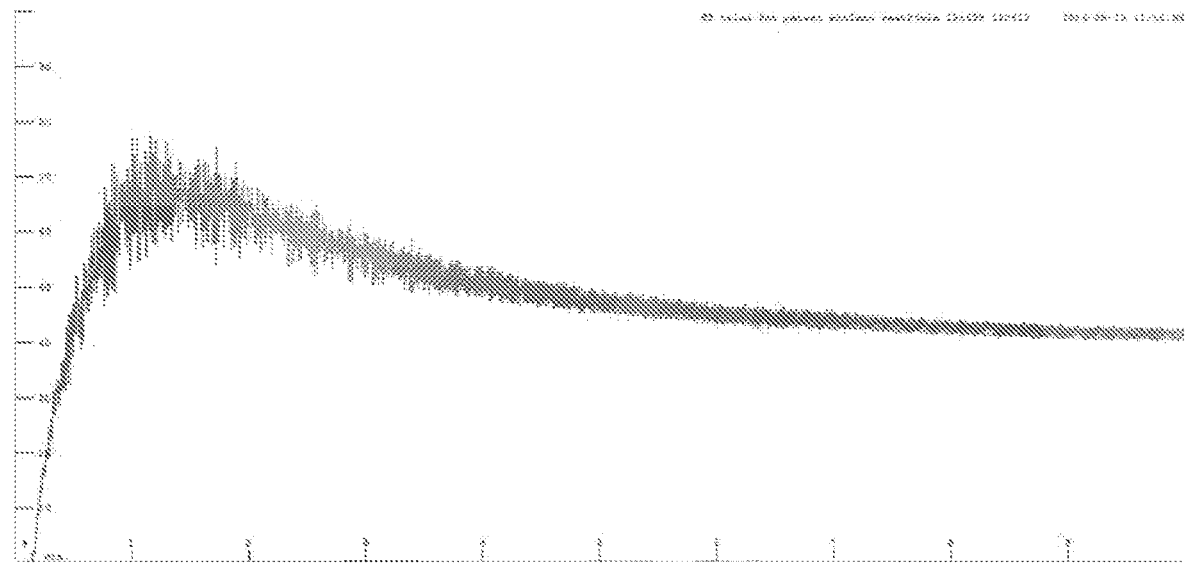
FIG. 2D shows the results of measuring changes with time in consistency by a mixograph test, for the powdered wheat proteins of Example 3-4.
Figure 3A:
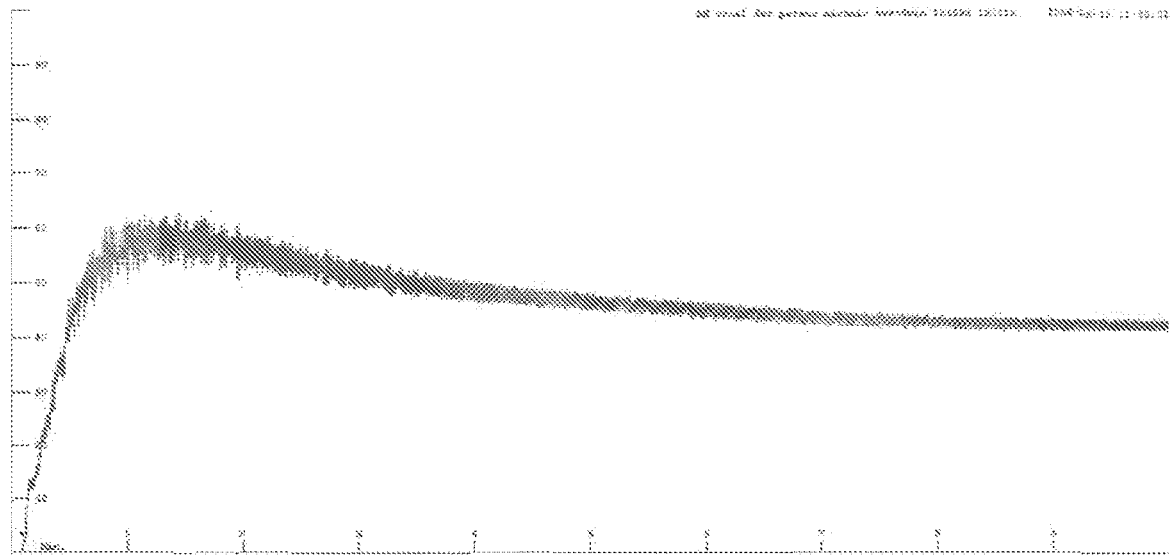
FIG. 3A shows the results of measuring changes with time in consistency by a mixograph test, for the powdered wheat proteins of Example 3-5.
Figure 3B:
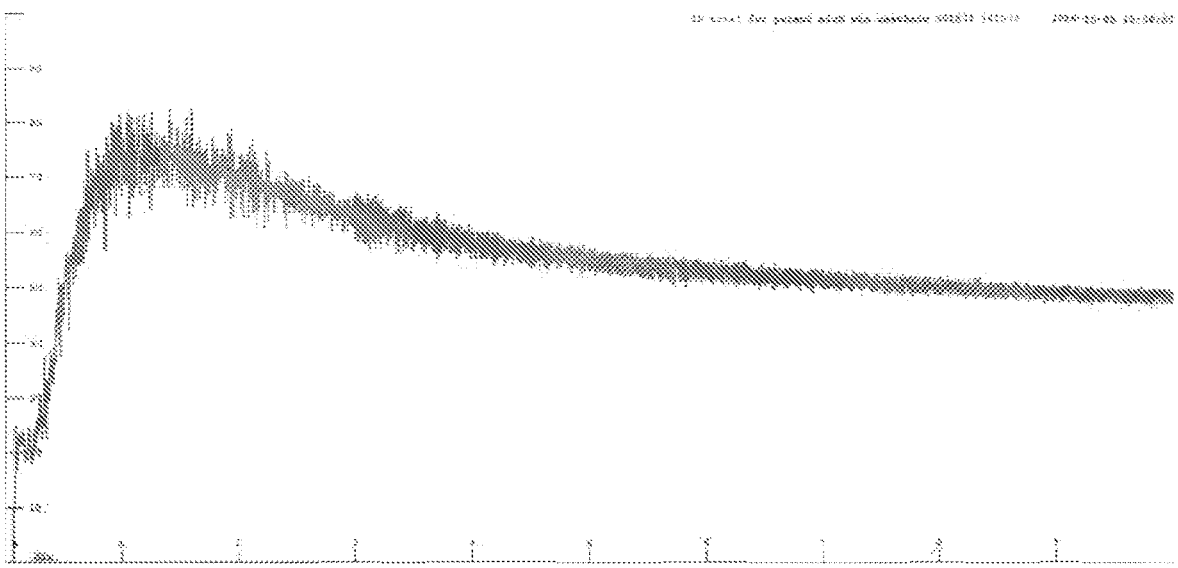
FIG. 3B shows the results of measuring changes with time in consistency by a mixograph test, for the powdered wheat proteins of Example 3 -6.
Figure 3C:
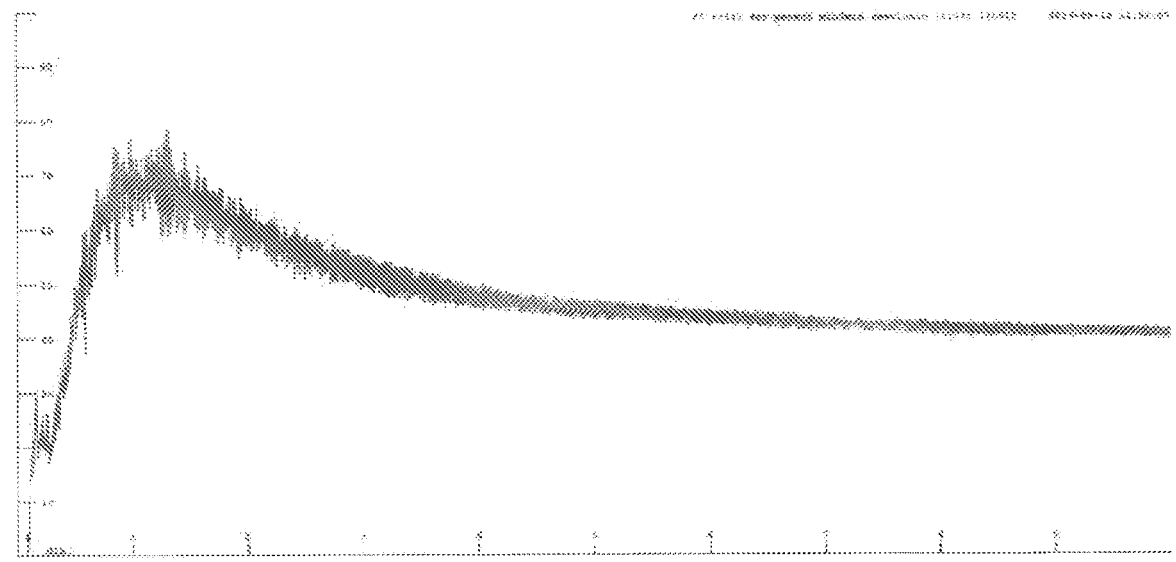
FIG. 3C shows the results of measuring changes with time in consistency by a mixograph test, for the powdered wheat proteins of Example 3 -7.
Figure 3D:
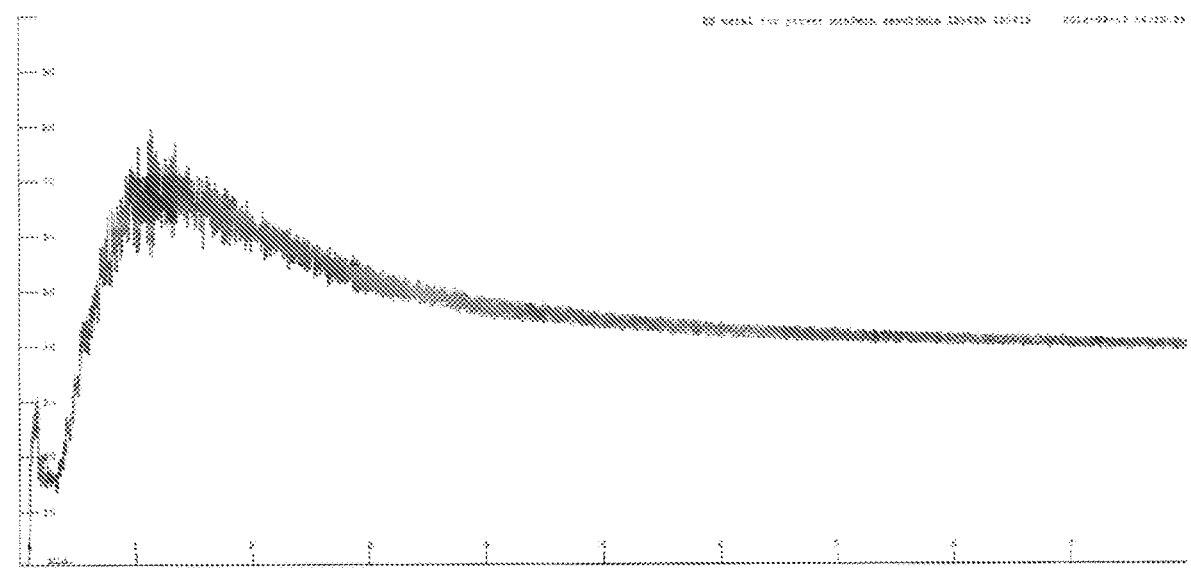
FIG. 3D shows the results of measuring changes with time in consistency by a mixograph test, for the powdered wheat proteins of Example 3-8.
Figure 4A:
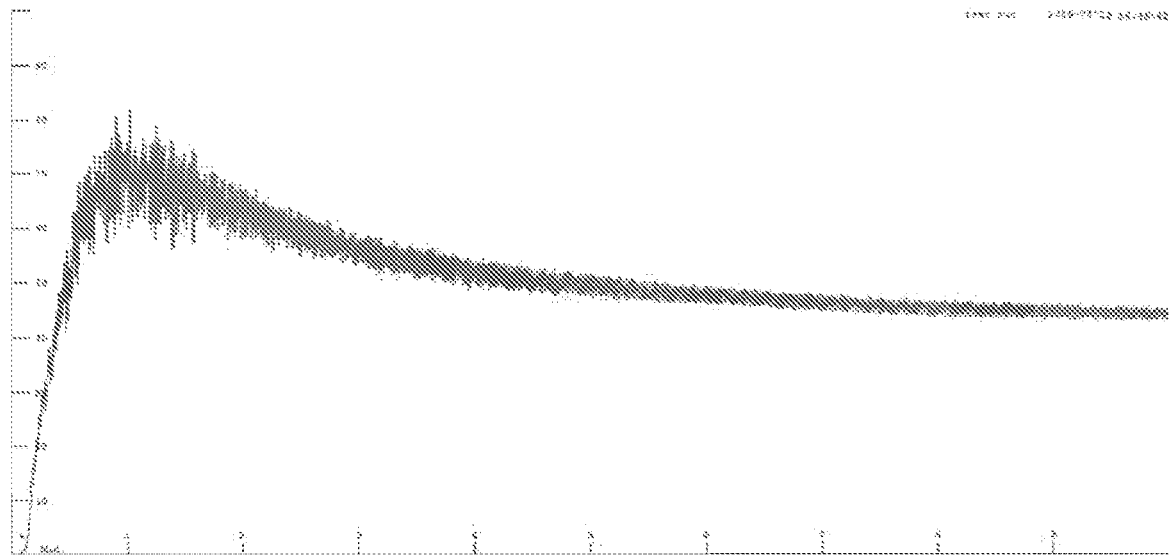
FIG. 4A shows the results of measuring changes with time in consistency by a mixograph test, for the powdered wheat proteins of Examples 3-9.
Figure 4B:
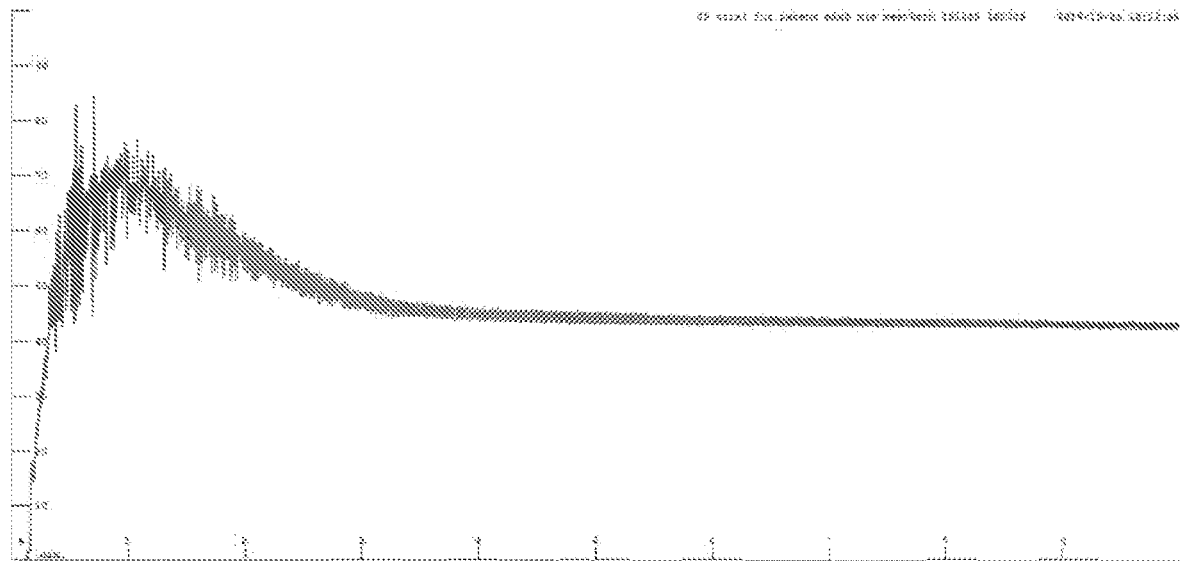
FIG. 4B shows the results of measuring changes with time in consistency by a mixograph test, for the powdered wheat proteins of Example 3-10.
Figure 4C:
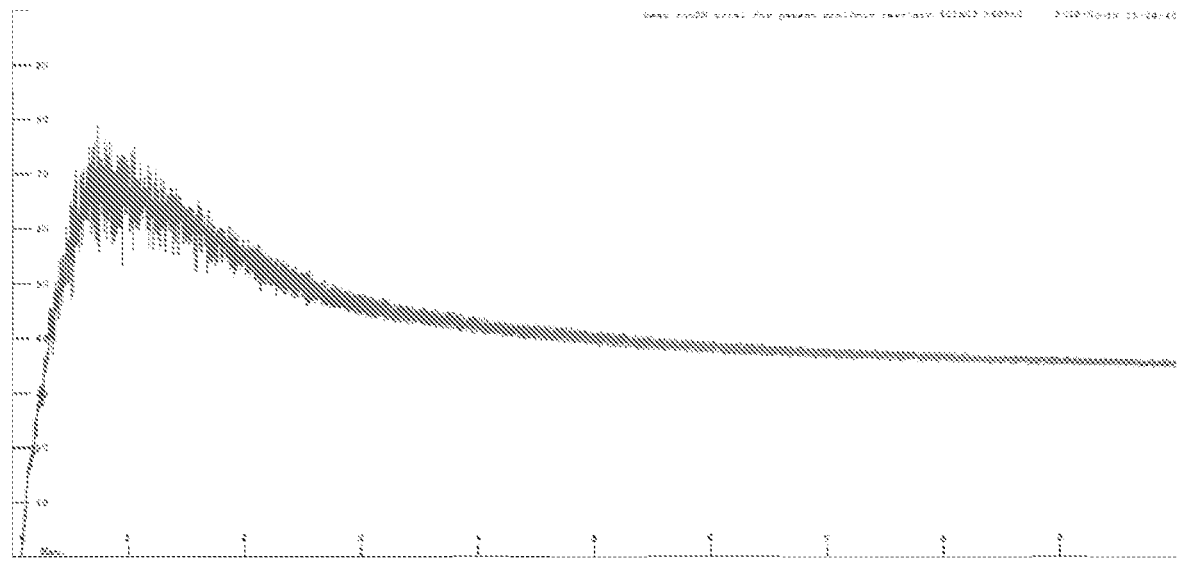
FIG. 4C shows the results of measuring changes with time in consistency by a mixograph test, for the powdered wheat proteins of Example 3-11.
Figure 4D:
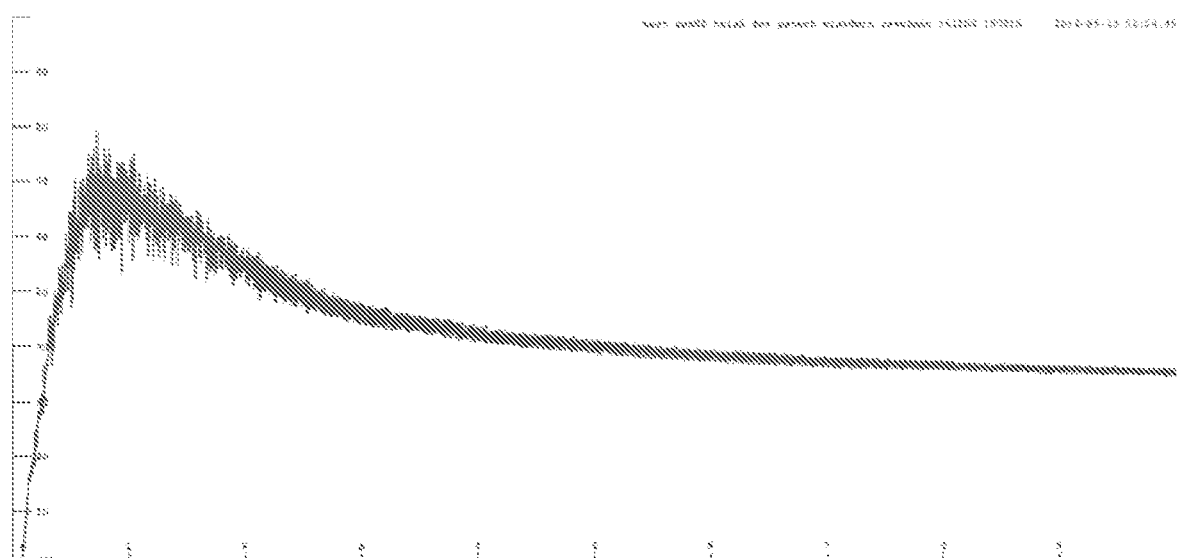
FIG. 4D shows the results of measuring changes with time in consistency by a mixograph test, for the powdered wheat proteins of Example 3-12.

Table 2 shows the results of measuring the loose bulk density and the packed bulk density, the results of determining the time to reach the maximum consistency and the gradient$_{(Max\text{-}After\ 5\ min)}$ by the mixograph test, and the results of determining the extension distance to break by the measurement of dough physical properties. Moreover, FIG. 1 shows the results of measuring changes with time in consistency by the mixograph test. These results have revealed that the powdered wheat protein of Example 2 has a loose bulk density and a packed bulk density similar to those of the commercially available product produced by drying by flash drying (Comparative Example 2-1), and has significantly reduced bulkiness, compared to that in the commercially available product produced by drying by spray drying (Comparative Example 2-2). The results have also revealed that the powdered wheat protein of Example 2 has a time to reach the maximum consistency of 5 minutes or less in the mixograph test, and can significantly accelerate the formation of dough, compared to the commercially available product formed by drying by flash drying (Comparative Example 2-1). Moreover, the results have revealed that the dough produced using the powdered wheat protein of Example 2 has extensibility higher than that of the dough produced using the commercially available product produced by drying by flash drying (Comparative Example 2-1).

Test Example 3

The following test was performed to ascertain the influence of the kneading time during the preparation of the pasty raw material and the standing time for the prepared pasty raw material, upon the physical properties of the powdered wheat protein produced.

To 100 g of wet gluten prepared using the same method as that in Test Example 1 above, 0.8 g of an aqueous acid solution containing 0.11 mol/L of lactic acid and 0.13 mol/L of acetic acid was added, and the mixture was kneaded using a mixograph for each of the predetermined times shown in Table 3 to obtain a pasty raw material. The resulting pasty raw material was allowed to stand at 25° C. for each of the predetermined times shown in Table 3. The pasty raw material after being allowed to stand was quickly frozen and dried by freeze drying, and then made into a powder using a grinding machine to obtain a powdered wheat protein.

For each of the obtained powdered wheat proteins, the loose bulk density and the packed bulk density were measured using the same method as that in Test Example 1 above, and the mixograph test was performed using the same method as that in Test Example 2 above.

Table 3 shows the results of measuring the loose bulk density and the packed bulk density, and the results of determining the time to reach the maximum consistency and the gradient$_{(Max\text{-}After\ 5\ min)}$ by the mixograph test. Moreover, FIGS. 2 to 4 shows the results of measuring changes with time in consistency by the mixograph test. The results have ascertained that all the powdered wheat proteins of Examples 3-1 to 3-12 have high bulk densities, and have a time to reach the peak consistency of 5 minutes or less. Moreover, the kneading time during the preparation of the pasty raw material had little influence on the gradient$_{(Max\text{-}After\ 5\ min)}$ in the mixograph test. However, when the standing time for the pasty raw material was 5 minutes or more, the gradient$_{(Max\text{-}After\ 5\ min)}$ became −4.00 Tq %/minute or less, and the physical properties of the powdered wheat proteins produced were clearly different between the case where the standing time for the pasty raw material was set to 5 minutes or more and the case where the standing time for the pasty raw material was set to be shorter than that. That is, the results have also revealed that the powdered wheat proteins produced by setting the standing time for the pasty raw material to 5 minutes or more can be used to control the dough to range from a firm one to a soft one, depending on the mixing time, and can be imparted with a variety of physical properties.

TABLE 2

|  | Production Method | Bulk Densities (g/100 cm³) | | Mixograph Test | | Measurement of Dough Physical Properties |
|---|---|---|---|---|---|---|
|  |  | Loose Bulk Density | Packed Bulk Density | Time to Reach Maximum Consistency (min) | Gradient$_{(Max\text{-}After\ 5\ min)}$ (tq %/min) | Extension Distance (mm) to Break |
| Example 2 | Produced by drying the pasty raw material after being allowed to stand, by flash drying | 52.0 | 67.1 | 2 | −3.056 | 27.20 |
| Comparative Example 2-1 | Produced by drying the pasty raw material by flash drying | 52.4 | 73.9 | 10 | −3.968 | 21.94 |
| Comparative Example 2-2 | Produced by drying the liquid raw material by spray drying | 35.8 | 53.9 | 1 | −1.937 | 35.20 |

TABLE 3

| | Production conditions | | Bulk Densities (g/100 cm³) | | Mixograph Test | |
|---|---|---|---|---|---|---|
| | Kneading Time (min) for Pasty Raw Material | Standing Time (min) for Pasty Raw Material | Loose Bulk Density | Packed Bulk Density | Time (min) to Reach Peak Consistency | Gradient$_{(Max\text{-}After\ 5\ min)}$ (tq %/min) |
| Example 3-1 | 1 | 0 | 43.6 | 65.5 | 1.56 | −3.607 |
| Example 3-2 | 1 | 5 | 40.7 | 61.1 | 1.37 | −4.936 |
| Example 3-3 | 1 | 10 | 45.7 | 64.8 | 1.30 | −5.003 |
| Example 3-4 | 1 | 20 | 41.8 | 62.2 | 1.46 | −4.448 |
| Example 3-5 | 3 | 0 | 42.1 | 62.3 | 1.46 | −2.753 |
| Example 3-6 | 3 | 5 | 43.2 | 64.7 | 1.39 | −4.297 |
| Example 3-7 | 3 | 10 | 43.5 | 65.1 | 1.24 | −4.535 |
| Example 3-8 | 3 | 20 | 42.9 | 62.7 | 1.38 | −4.679 |
| Example 3-9 | 5 | 0 | 44.3 | 63.5 | 1.22 | −3.728 |
| Example 3-10 | 5 | 5 | 51.4 | 74.1 | 1.09 | −4.033 |
| Example 3-11 | 5 | 10 | 45.2 | 64.1 | 1.03 | −4.916 |
| Example 3-12 | 5 | 20 | 43.7 | 61.5 | 1.03 | −5.052 |

The invention claimed is:

1. A powdered wheat protein having a loose bulk density of 50 g/100 cm³ or more, and having a time to reach a maximum consistency of 5 minutes or less in a mixograph test under the following conditions:

<conditions for the mixograph test>

10 g of the powdered wheat protein, 20 g of acetylated wheat starch (degree of substitution (DS): 0.02), and 28 g of water (15° C.) are kneaded at a temperature of 25° C., using a 35-g mixograph (stirring-type viscoelasticity measuring apparatus), based on the AACC method 54-40.02 defined by AACC (American Association of Cereal Chemists), and consistency of the resulting material is measured with time;

wherein the powdered wheat protein is obtained by a method comprising:

step 1 of preparing a pasty raw material formed by kneading a wheat protein, an acid, and water, wherein a moisture content in the pasty raw material is 15 to 60% by mass; and step 2 of drying the pasty raw material obtained in step 1 by freeze drying or flash drying.

2. The powdered wheat protein according to claim 1, wherein a packed bulk density is 60 g/100 cm³ or more.

3. The powdered wheat protein according to claim 1, wherein in the mixograph test under said conditions, a gradient$_{(Max\text{-}After\ 5\ min)}$ calculated based on the following equation, using a consistency at the time to reach the maximum consistency ($V_{max}$) and a consistency at 5 minutes after the time to reach the maximum consistency ($V_{5\ min\ after\ Xmax}$), is −2.00 tq %/minute or less:

$$\text{gradient}_{(Max\text{-}After\ 5\ min)} = (V_{max} - V_{5\ min\ after\ Xmax})/5. \quad [\text{Expression 1}]$$

4. A processed food comprising the powdered wheat protein according to claim 1.

5. The processed food according to claim 4, which is a noodle.

6. A method for producing a powdered wheat protein comprising:

step 1 of preparing a pasty raw material formed by kneading a wheat protein, an acid, and water; and step 2 of drying the pasty raw material obtained in step 1 by freeze drying or flash drying;

wherein a moisture content in the pasty raw material prepared in step 1 is 15 to 60% by mass;

wherein the produced powdered wheat protein has a loose bulk density of 40 g/100 cm³ or more, and has a time to reach a maximum consistency of 5 minutes or less in a mixograph test under the following conditions:

<conditions for the mixograph test>

10 g of the powdered wheat protein, 20 g of acetylated wheat starch (degree of substitution (DS): 0.02), and 28 g of water (15° C.) are kneaded at a temperature of 25° C., using a 35-g mixograph (stirring-type viscoelasticity measuring apparatus), based on the AACC method 54-40.02 defined by AACC (American Association of Cereal Chemists), and consistency of the resulting material is measured with time.

7. The method for producing a powdered wheat protein according to claim 6, wherein the pasty raw material obtained in step 1 is allowed to stand for 5 minutes or more, and then subjected to step 2.

8. The method for producing a powdered wheat protein according to claim 6, wherein an acid content in the pasty raw material prepared in step 1 is 0.01 to 0.50 mol/kg.

* * * * *